United States Patent [19]

Schmidt, III

[11] Plant 5,003

[45] Mar. 22, 1983

[54] FLOWERING PLUM TREE

[76] Inventor: J. Frank Schmidt, III, 14131 SE. 312th, Boring, Oreg. 97009

[21] Appl. No.: 275,716

[22] Filed: Jun. 22, 1981

[51] Int. Cl.[3] ..... A01H 5/12

[52] U.S. Cl. ..... Plt./37

[58] Field of Search ..... Plt./37

*Primary Examiner*—Robert E. Bagwill

*Attorney, Agent, or Firm*—Klarquist, Sparkman, Campbell, Leigh, Whinston & Dellett

[57] ABSTRACT

This invention relates to a novel variety of Cistena Plum tree, distinguished by its more vigorous growth rate and larger foliage.

1 Drawing Figure

The present invention relates to a new and distinct variety of flowering plum tree of the species botanically known as *Prunus cistena* and commonly called "Cistena Plum."

I discovered my new variety, believed to be the result of a bud sport, among a group of nursery plants of the Cistena Plum variety, which were being grown from cuttings in the cultivated area of a nursery in Boring, Oreg. Among this group, which comprised several thousand two-year-old Cistena Plum plants, I noticed my new tree because it was approximately eighteen inches taller than other plants in the group.

Close observation of the parent tree, and asexual reproduction of the parent tree under my direction to produce progeny thereof, continued observations of such progeny, which possessed identical characteristics so far as observable, and which were subsequently asexually propagated under my direction and control, has convinced me that my new tree represents a new and improved variety of Cistena Plum tree. Furthermore, these observations have confirmed that my new variety is particularly evidenced by the following unique combination of characteristics, which have proven firmly fixed, are outstanding therein, and which distinguish it from all other varieties of this species of which I am aware:

1. A rapid, vigorous rate of growth; and
2. Extremely large foliage.

In determining the above characteristics, I have compared my new tree with common Cistena Plum trees which were growing under the same conditions in a nursery plot located near Canby, Oreg.

The accompanying photographs depict the color of the foliage of my new variety as nearly true as is reasonably possible to make the same in a color illustration of this character.

FIG. 1 is a color photograph of a portion of a tree of the present invention taken during the spring of 1980.

The primary distinguishing feature of my new tree, over other trees of this species, is its much more vigorous rate of growth. In the past, common Cistena Plum trees have typically been used as shrubs, because of their relatively slow growth rate. However, because of its rapid growth rate, my new variety is more usable as a tree.

Continued visual observations of my new variety of Cistena Plum tree and common Cistena Plum trees, over a number of years, has confirmed the distinctiveness of the growth rate of my new variety. In addition to such visual observations, during the 1980 growing season, spring and summer, measurements were made of the growth of trees of my new variety of Cistena Plum tree and of the growth of common Cistena Plum trees of the same age. These measurements were made of trees of my new variety and of the common variety which were growing in the same row in a nursery. All of these trees were budded about two years earlier on Myrobalam Prunus (*Prunus myrobalana,* otherwise known as *Prunus cerasifera*) understock.

More specifically, in mid-November of 1980, the caliper of twelve trees of the common variety were measured at a point approximately three inches above the location of budding to the understock. The average caliper of these trees was approximately 1.3 centimeters. Similar measurements were made of the caliper of twenty-five trees of my new Cistena Plum variety, growing in the same row. The average caliper of these trees of my new variety was 2.0 centimeters.

In addition, measurements were made on June 4, July 7, Aug. 4 and Sept. 4, 1980. Measurements were made of the length of side branches of my new variety of Cistena Plum tree and of the length of side branches of common Cistena Plum trees. On each date, fifty branches from trees of my new variety were measured. Also, on each date, fifty branches from trees of the common variety were measured. These branches were located at approximately the same position on the trees. Again, the trees were located in the same row of a nursery. The following table summarizes the average of these measurements.

AVERAGE LENGTH OF SIDE BRANCHES

| DATE | NEW CISTENA PLUM TREE | COMMON CISTENA PLUM TREE |
|---|---|---|
| June 4, 1980 | 60.9 cm | 27.2 cm |
| July 7, 1980 | 69.8 cm | 31.7 cm |
| August 4, 1980 | 83.3 cm | 43.3 cm |
| Sept. 4, 1980 | 80.1 cm | 43.4 cm |

Thus, although only a limited number of samples were taken, the measurements confirm my observations thay my new Cistena Plum tree is a much faster growing tree than common Cistena Plum trees.

Also, the foliage of my new tree is larger than the foliage of common Cistena Plum trees. In addition to my visual observations, during the 1980 growing season, measurements and comparisons were made of the size of foliage of my new tree with the size of foliage of common Cistena Plum trees growing in the same row of a nursery. Although there was some variation from leaf to leaf, typical leaves of my new Cistena Plum tree averaged 92 millimeters long and 43 millimeters wide. In contrast, leaves of the common Cistena Plum trees had typical average lengths of 80 millimeters long and 35 millimeters wide. This larger foliage of my tree enhances its suitability for ornamental and decorative purposes.

Otherwise, insofar as I have been able to observe at this time, my new variety is believed generally typical of the species.

The following is a detailed description of my new variety of *Prunus cistena* tree, with color terminology in accordance with The Royal Horticultural Society Colour Chart (hereinafter R.H.S.), published by The Royal Horticultural Society of London. It is pointed out, however, that the size and shape of leaves varies depending upon the nature of the growing season.

Parentage: A bud sport of *Prunus cistena.*

Propagation: Holds to distinguishing characteristics through succeeding propagation by budding on Myrobalam Plum understock.

Locality where grown and observed: Boring, Oreg. and Canby, Oreg.

Tree: Upright, rapid growing.

Foliage:

*Shape.*—Generally elliptic.

*Apex.*—Accuminate.

*Base.*—Cuneate.

*Margin.*—Serrulate.

*Size.*—Typically 92 mm long and 43 mm broad.

*Color.*—Typical of the species, in the fall being like R.H.S. plates 187A through 187B.

I claim:

1. A new and distinct variety of flowering plum tree substantially herein shown and described, characterized particularly as to novelty by its vigorous rate of growth and large foliage.

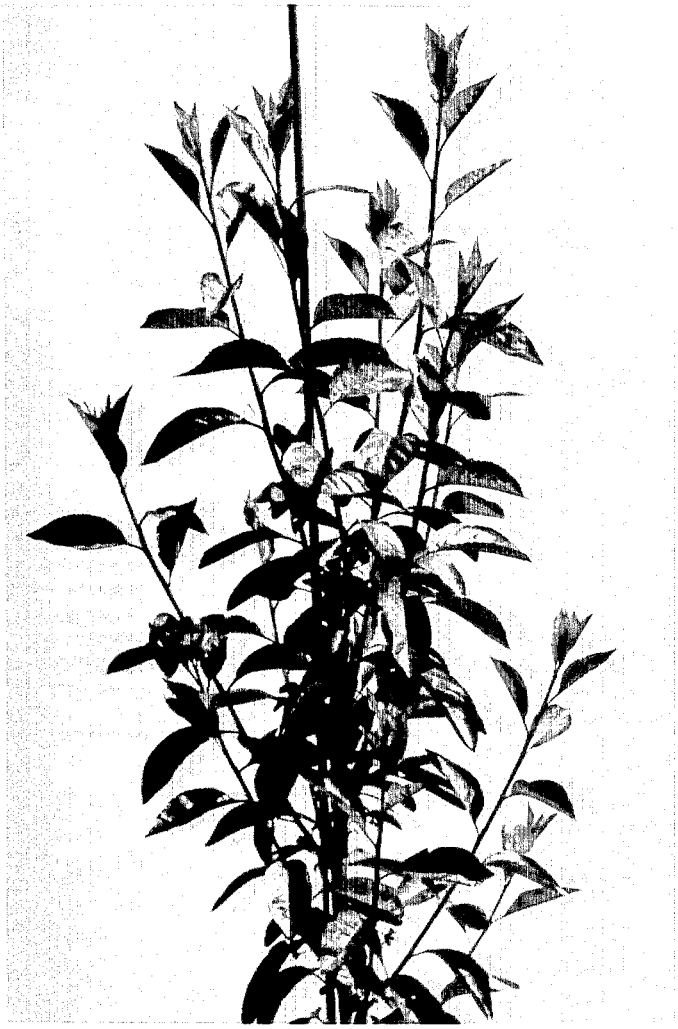

* * * * *